US006254789B1

(12) United States Patent
Marion et al.

(10) Patent No.: US 6,254,789 B1
(45) Date of Patent: Jul. 3, 2001

(54) METHOD FOR TREATING AQUEOUS SOLUTIONS COMPRISING ACIDS AND NITRATED COMPOUNDS

(75) Inventors: Philippe Marion, Vernaison; Louis Le Bris, Lyons; Gérard Berrod, Villeurbanne; Georges Dovergne, Le Pont de Claix; Philippe Perrona, Charly, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/485,498
(22) PCT Filed: Aug. 11, 1998
(86) PCT No.: PCT/FR98/01793
§ 371 Date: May 3, 2000
§ 102(e) Date: May 3, 2000
(87) PCT Pub. No.: WO99/08995
PCT Pub. Date: Feb. 25, 1999

(30) Foreign Application Priority Data

Aug. 13, 1997 (FR) .................................................. 97 10346

(51) Int. Cl.$^7$ ....................................................... C02F 1/04
(52) U.S. Cl. ......................... 210/765; 210/790; 210/805; 210/806; 210/903; 210/909
(58) Field of Search ..................................... 210/749, 765, 210/790, 805, 806, 194, 903, 909

(56) References Cited

U.S. PATENT DOCUMENTS

| 2,773,911 | 12/1956 | Dubois ................................. 260/645 |
| 5,554,299 | * 9/1996 | Joulak et al. . |
| 5,696,305 | * 12/1997 | Klingler et al. . |
| 5,820,764 | * 10/1998 | Joulak et al. . |

FOREIGN PATENT DOCUMENTS

| 0 047 331 | 3/1982 | (EP) .............................. C07C/76/06 |

* cited by examiner

*Primary Examiner*—David A. Simmons
*Assistant Examiner*—Betsey Morrison Hoey
(74) *Attorney, Agent, or Firm*—Jean-Louis Seugnet

(57) ABSTRACT

The invention concerns a method for treating an aqueous solution derived from sluicing of crude mononitrated or dinitrated aromatic compounds obtained by nitration of the corresponding aromatic compounds, consisting in: (a) contacting said aqueous solution with said aromatic compound thereby obtaining an aqueous phase and an organic phase; (b) recycling said organic phase in the nitration process; (c) distilling said aqueous phase; (d) recycling the resulting concentrated acid solution in the nitration process; (e) recycling or eliminating the recuperated water after distillation.

13 Claims, No Drawings

METHOD FOR TREATING AQUEOUS SOLUTIONS COMPRISING ACIDS AND NITRATED COMPOUNDS

This application is an application under 35 U.S.C. Section 371 of International Application Number PCT/FR98/01793, filed on Aug. 11, 1998.

The process of the invention relates to treating aqueous solutions from washes, more particularly from acid washes from nitroaromatic compounds.

Processes for preparing nitroaromatic compounds, more particularly dinitro-aromatic compounds, have been employed industrially for many years, Such compounds are intermediates in the preparation of aromatic diamines, these latter being used to synthesise the corresponding isocyanates. The isocyanates are then used to synthesise polyurethanes, which have many applications.

Briefly, dinitration reactions are usually carried out in two steps, the first consisting of preparing mononitro compounds, and the second consisting of preparing the dinitro compounds. In addition to the aromatic compound to be reacted, a nitrating acid is used, generally a nitric acid/sulphuric acid mixture, the sulphuric acid being the catalyst for the reaction.

At the end of the nitration step, the nitro compound is separated from the residual acid. That operation is usually carried out by direct decantation of or by centrifuging the reaction mixture.

The nitro compounds obtained after separating the nitrating acid (also known as crude nitro compounds) cannot be used as they are unless they are intended to be nitrated again. They still contain a fraction of the nitrating acid in the dissolved state, as well as organic impurities.

It should be noted that nitration reactions carried out using nitric acid alone as the nitrating acid cause the same difficulties with purification of the nitro compounds obtained.

The aromatic nitro compounds which are separated from the residual acid also contain a fraction of nitric acid representing several percent by weight of the nitro compounds, which must be recovered. They also contain organic by-products which have to be eliminated.

Such problems, connected with purifying the aromatic nitro compounds, and more particularly to the separation and recovery of the dissolved acids, have formed the basis of a number of studies.

The recovery of residual acids has non negligible economic consequences, given the tonnages of nitro compounds. Further, their recovery also has an impact on the environment as it can limit aqueous discharges. In addition, acid recovery can reduce the cost of treating residual water which cannot be discharged as it is, as it is polluted with salts such as sulphates and in particular nitrates.

Methods for separating and recovering dissolved nitric and sulphuric acids are all directed towards improving the efficiency of the various nitro compound washes.

In a first possibility, described in European patent EP-A-0 279 312, crude dintrotoluene is washed with a very small amount of water. In this way, the wash water, charged with nitric and sulphuric acids, is sufficiently concentrated to enable it to be returned directly to the nitration process. However, such a method has the disadvantage of requiring the use of a particular apparatus to separate the aqueous and organic phases, in that instance a coalescer. Because of the very small amount of water used for washing, decantation is difficult. Further, the extraction yields are at most 72%.

A further possibility, constituting the subject matter of European patent application EP-A-0 736 514, consists of washing the crude dinitrotoluene with the water charged with the acids used for the nitration reaction in a plurality of counter-current steps. The water which is recovered can be recycled to the nitration process, without prior concentration, or preferably with prior concentration of the acid water. That process, however, does not satisfy all the necessary safety requirements. The acid water concentration step, which is necessary in the majority of cases, is associated with a number of risks, as the aqueous phase to be distilled contains both nitrating acids and dissolved dinitrotoluene. As a result, dinitrotoluene nitration conditions are satisfied, resulting in trinitrotoluene, the particular properties of which are well known. Further, the dinitrotoluenes present in the aqueous acidic phase from washing are not recovered in the case where that water is concentrated. Such compounds are entrained with the water during distillation and are lost. Further still, the nitro compounds can cause blockages or soiling in the concentration column as they are condensed at the column head and thus solidify. They can also be found in the water intended for discharge, thus causing pollution or oxvercosts as they have to be eliminated.

Thus the subject matter of the present invention is the recovery of the acid or acids contained in crude nitro compounds by carrying out a simple and efficient process with maximum safet during implementation.

Further, the process of the invention enables nitroaromatic compounds which would be dissolved in the aqueous phase from washing the crude nitro compounds to be recovered.

The invention thus provides a process for treating an aqueous solution originating from washing mononitro or dinitro aromatic compounds obtained by reacting a corresponding aromatic compound with a nitrating acid comprising at least nitric acid, said mononitro or dinitro aromatic compounds having been separated from the aqueous acid phase prior to said washing. The process of the invention is characterized in that the following steps are carried out:

(a) said aqueous solution is brought into contact with said aromatic compound to obtain an aqueous phase and an organic phase;

(b) said organic phase is recycled to the nitration process;

(c) said aqueous phase is distilled;

(d) the concentrated acid obtained is recycled to the nitration process;

(e) the water recovered after distillation is recycled or eliminated.

Further characteristics and advantages of the present invention will become clear from the following description.

As indicated above, the process of the invention is particularly suitable for treating aqueous solutions from aromatic compound nitration processes.

Aromatic compounds which can be nitrated can comprise one or more aromatic rings. Suitable examples are benzene and its derivatives, naphthalene and its derivatives, phenanthrene and its derivatives, biphenyl, diphenyl oxide and their derivatives.

The term "derivatives" means aromatic radicals comprising one or more substituents, such as $C_1$–$C_6$ alkyl radicals or $C_3$–$C_6$ cycloalkyl radicals; hydroxyl radicals: $C_1$–$C_5$ alkoxy radicals: $C_1$–$C_2$ aminoacyl radicals; and halogen atoms;

Non limiting examples of alkyl or cycloalkyl radicals which can be cited are methyl, ethyl, n-propyl. isopropyl, n-butyl, isobutyl, tertiobutyl, n-hexyl and cyclohexyl.

Examples of alkoxy radicals which can be cited are methoxy, ethoxy and propoxy.

Aminoacyl radicals include acetylamine and benzoylamine radicals.

Fluorine, chlorine, bromine and iodine are suitable halogens.

The aromatic compound which is preferably used in the nitration reactions is selected from benzene, toluene, xylene and its isomers, ethylbenzene, propylbenzene, isopropylbenzene, chlorobenzene, chloromethylbenzene, chloroethylbenzene, biphenyl and diphenyl oxide.

In a particular implementation, the flow which is treated in accordance with the present invention originates from benzene nitration, i.e., mononitrobenzene or different dinitrobenzene isomers. The process of the invention is particularly suitable for treating aqueous solutions originating from washing compounds obtained from benzene nitration, i.e., the different isomers of mononitrotoluene, preferably dinitrotoluene.

It should be noted that the present invention is also suitable for treating aqueous solutions originating from washing the aromatic compounds cited above, which have undergone trintration.

Before going on to describe details of the process of the invention, the manner in which the aqueous solutions to be treated in accordance with the invention must be described.

Firstly, the process of the invention is perfectly suited to treating nitro compounds obtained using nitric acid alone, or a nitrosulphuric acid mixture as the nitrating mixture.

When nitric acid is used alone, the nitro compounds are separated from the acid in two stages. Firstly a salt selected from nitrates is introduced into the reaction mixture then the mixture plus additive is partially evaporated. It then becomes possible to separate the nitro compounds from the aqueous phase, which comprises nitric acid and nitrate, by decanting.

When nitration is carried out in the presence of a nitrosulphuric mixture separation is immediate using known means such as simple decanting or centrifuging.

Reference will be made below to nitro compounds obtained using a nitrosulphuric mixture as the nitrating acid. Clearly, anything indicated for a nitrating mixture remains valid if only nitric acid is used for the nitration reaction.

The nitro compounds obtained, termed crude nitro compounds, are then brought into contact with a washing medium comprising water (acid washing). This operation is intended to separate the crude compounds, and small quantities of nitrating acid which are soluble or entrained during decantation.

Acid washing usually comprises a plurality of steps to increase the extraction efficiency.

It should also be noted that the washing medium used during an acid washing step is water-based, but it can also comprise traces of nitrating acid. These traces of nitrating acid may have been extracted, for example during the previous stages of the same acid washing step (using the washing medium from step n-1 in step n) or may originate from recycling a fraction of the washing medium from the same acid washing step (loop) to the step in question.

In a first implementation, the washing operation is carried out in an extraction column. In this implementation, the column comprises 1 to 6 theoretical plates. In this case, counter-current washing is carried out, the crude nitro compounds and washing medium being supplied to opposite extremities of the column.

In a second implementation, washing is carried out in at least one mixer-settler apparatus. When a plurality of units of this type are used, counter-current washing is preferably carried out so as to improve the extraction efficiency.

In order to limit the quantity of washing medium while keeping the extraction conditions favourable, each mixer-settler unit preferably recycles a portion of the washing medium to the same unit, the other being supplied to a unit which is preferably upstream (operating in counter-current mode).

In order to preserve continuous operation, an amount of washing medium is usually added corresponding to the quantity of aqueous solution extracted for treatment in the process of the invention. It should be noted that the washing medium can be fresh water or water from any other point of the process such as a neutral aromatic nitro compound washing step.

The washing medium thus comprises at least water. In a more particular implementation, the washing medium comprises both water and nitrating acid. This situation occurs if counter-current washing has been carried out, as is the case for extraction columns, or when using a plurality mixer-settlers in series.

In either of these implementations, the overall amount of washing medium with respect to the nitro compounds to be washed is such that the weight ratio of the phase comprising the nitro compounds with respect to the water is in the range 1.5 to 6.

All of the wash variations must be carried out at a temperature which is higher than the melting point of the nitro compounds to be washed.

Once washing is complete, nitro compounds are recovered which then undergo the other Washing steps.

Conventionally, a basic wash is carried out. The aim of such an operation is to separate the nitro compounds, and organic by-products, which are mainly hydroxynitroaromatic compounds, by transforming them into salts which are then soluble in the aqueous phase. The base used can be selected from alkali metal hydroxides or from alkali metal carbonates. Reference should be made to European patent application EP-A-0 662 454 which describes such a basic wash.

At the end of the basic wash, it is also possible to carry out a final water wash (neutral wash to eliminate all traces of base used during the preceding wash. The resulting nitro compounds can then be hydrogenated using conventional methods.

The treatment in accordance with the invention of the aqueous solution from the first wash category, acid washing, will now be described.

The aqueous solution from this acid wash comprises aromatic nitro compounds and nitratino acid in addition to water.

In a first step (a), said aqueous solution is brought into contact with an aromatic compound. This aromatic compound is more particularly that which has been nitrated upstream. In other words, the aromatic compound used for extraction is that used for the mononitration reaction.

Contact can be carried out in an extraction column or in at least one mixer-settler.

When a column is used, the number of theoretical plates is more particularly in the range 2 to 10.

The aromatic compound and aqueous solution are supplied to each of the column extremities, the aqueous solution preferably being introduced to the column head, the aromatic compound being introduced to the bottom. Conventionally, supply is made to at least one plate above the first and to at least one plate below the last.

When the mixer-settler option is used, it is preferably used with at least two mixer-settler units, preferably in a series comprising 2 to 10 units.

Still more particularly, a portion of the flow of aromatic compound is recycled to the same mixer-settler unit, the other portion being supplied to a mixer-settler located upstream or downstream, depending on the operating mode selected, namely counter-current extraction or otherwise. In this case, and to maintain continuous operation, fresh aromatic compound is added. This addition is preferably carried out at the last stage of the wash or at the opposite end to that at which the aqueous phase is supplied to the column—operation in counter-current mode.

In a particular implementation of this option, counter-current extraction is carried out.

The quantity of aromatic compound used with respect to that of the aqueous solution to be reated can vary within a wide range. By way of illustration, the weight ratio of the aqueous solution to the aromatic compound is in the range 1/1 to 10/1.

This operation is normally carried out at a temperature of the order of 10° C. to 70° C. referably at a temperature in the range 40° C. to 60° C.

At the end of step (a), an organic phase comprising mainly the aromatic compound used as the extraction solvent is recovered, in which the fraction of nitroaromatic compounds which was resent in the aqueous solution at the start is dissolved.

Highly advantageously, said organic phase is recycled to the nitration process in a step (b). in a preferred implementation, which carries out a mono- or dinitration process, said organic phase is re-introduced to the mononitration step. As an example, said organic phase can be engaged in the mononitration reaction, or it can be used to extract residual mononitration acids, i.e., the aqueous acid phase obtained after decanting the reaction mixture from the mononitration stage.

Regarding the aqueous phase from step (a), i.e., obtained after bringing the aqueous solution from washing the crude nitro compounds into contact with the aromatic compound, it is distilled in a step (c). This operation concentrates the water comprising the acids.

It should be noted that this concentration operation can be carried out with no danger as the nitroaromatic compounds have already been extracted.

This concentration operation is carried out, as is conventional, in at least one distillation column. This column comprises a number of theoretical plates, in particular in the range 3 to 10.

In order to minimise energy costs, this concentration can be carried out in two columns. In a first column, part of the water is evaporated. In the second, water evaporation is continued until the desired acid concentration is obtained. This column is supplied with the liquid fraction recovered from the bottom of the preceding column, and heated by the heat recovered during condensation of the water at the head of the first column.

In this case, the first column advantageously comprises one theoretical plate, optionally two. The second is a column with at least three theoretical plates.

The column or columns advantageously operate under atmospheric pressure but vacuum operation of one and/or the other column is perfectly possible.

The process of the invention can produce acid solutions with a total acid concentration in the range 30% to 75%.

The concentrated solution comprising the acid is advantageously recycled to the nitration process proper (step (d)), whether this be a mononitration step or a dinitration step.

The effluent water recovered overhead from step (c) can be discharged as it is but it can also recycled to the step for washing the crude nitroaromatic compounds (step (e)), whether mononitrated or dinitrated.

What is claimed:

1. A process for treating an aqueous solution originating from washing mononitro- or dinitro-aromatic compounds obtained by a nitration step comprising the reaction of a corresponding aromatic compound with a nitrating acid comprising at least nitric acid, said mononitro- or dinitro-aromatic compounds having been separated from the aqueous phase prior to said washing, said washing being carried out with water, optionally comprising traces of nitrating acid, said process comprising the following steps:
   (a) mixing said aqueous solution with said aromatic compound to obtain an aqueous phase and an organic phase;
   (b) recycling said organic phase to the nitration step;
   (c) distilling said aqueous phase to obtain a concentrated acid;
   (d) recycling the concentrated acid obtained in step (c) to the nitration step;
   and
   (e) recycling or eliminating the water recovered in step (c).

2. A process according to claim 1, wherein step (a) is carried out in an extraction column, or in at least one mixer-settler unit.

3. A process according to claim 2, wherein the aqueous solution is supplied to the column head and the aromatic compound is supplied to the column bottom.

4. A process according to claim 2, wherein a portion of the aromatic compound is recycled to the same mixer-settler unit, the other portion being supplied to a mixer-settler located upstream or downstream depending on whether the operating mode selected is counter-current extraction or otherwise.

5. A process according to claim 4, wherein step (a) is carried out in at least two mixer-settler units operating in counter-current mode.

6. A process according to claim 1, wherein step (a) is carried out at a temperature in the range 10° C. to 70° C.

7. A process according to claim 6, wherein the temperature is in the range 40° C. to 70° C.

8. A process according to claim 1, wherein step (a) is carried out with a weight ratio of the aqueous solution to the aromatic compound in the range 1/1 to 10/1.

9. A process according to claim 1, wherein the distillation of step (c) is carried out in at least one column.

10. A process according to claim 9, wherein the distillation is carried out to obtain a solution of acids with a total acid concentration in the range 30% to 75%.

11. A process according to claim 9, wherein the distillation of step (c) is carried out in two columns:
   a first column in which a portion of the water is evaporated; and
   a second column in which evaporation is continued until the desired acid concentration is obtained, being supplied with the liquid fraction recovered from the bottom of the preceding column, and heated by the heat recovered on condensing water from the head of the first column.

12. A process according to claim 1, wherein said mononitro- or dinitro-aromatic compounds are mononitrobenzene, dinitrobenzene, the isomers of dinitrobenzene, mononitrotoluene, dinitrotoluene or the isomers of dinitro toluene.

13. A process according to claim 1, wherein in step (a) the aromatic compound is benzene or toluene.

* * * * *